(12) United States Patent
Peterson

(10) Patent No.: US 7,153,308 B2
(45) Date of Patent: Dec. 26, 2006

(54) UNIVERSAL ATTACHMENT MECHANISM FOR ATTACHING A SURGICAL TRACKING DEVICE TO AN INSTRUMENT

(75) Inventor: Thomas Herbert Peterson, Wilmington, MA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 402 days.

(21) Appl. No.: 10/437,533

(22) Filed: May 14, 2003

(65) Prior Publication Data

US 2004/0230200 A1    Nov. 18, 2004

(51) Int. Cl.
*A61B 17/56* (2006.01)
*A61B 19/00* (2006.01)

(52) U.S. Cl. ........................... 606/96; 606/130

(58) Field of Classification Search ............... 606/96, 606/97, 98, 102, 130; 600/104, 111, 112, 600/202, 221

See application file for complete search history.

(56) References Cited

U.S. PATENT DOCUMENTS

| | | | | |
|---|---|---|---|---|
| 4,237,871 A | * | 12/1980 | Bonnet | 600/104 |
| 4,802,479 A | * | 2/1989 | Haber et al. | 606/192 |
| 5,251,613 A | * | 10/1993 | Adair | 600/109 |
| 5,624,447 A | * | 4/1997 | Myers | 606/96 |
| 6,071,233 A | * | 6/2000 | Ishikawa et al. | 600/104 |
| 6,712,849 B1 | * | 3/2004 | Re et al. | 623/13.14 |
| 6,921,404 B1 | * | 7/2005 | Bimman | 606/96 |
| 6,932,823 B1 | * | 8/2005 | Grimm et al. | 606/130 |
| 2002/0151894 A1 | * | 10/2002 | Melkent et al. | 606/61 |

* cited by examiner

*Primary Examiner*—Eduardo C. Robert
*Assistant Examiner*—David Comstock
(74) *Attorney, Agent, or Firm*—McAndrews, Held & Malloy, Ltd.; Peter J. Vogel; Michael A. Dellapenna

(57) ABSTRACT

An attachment mechanism for attaching a component to an instrument. The attachment mechanism includes a first hoop assembly having a first hoop receiving a first portion of the instrument and a second hoop assembly having a second hoop receiving a second portion of the instrument. Either one of the first hoop assembly or the second hoop assembly may be configured to retain the component thereto. The first and second hoop assemblies are configured to be secured to each other such that the first and second hoops are in tension with, and secured about, the instrument.

18 Claims, 4 Drawing Sheets

UNIVERSAL ATTACHMENT MECHANISM FOR ATTACHING A SURGICAL TRACKING DEVICE TO AN INSTRUMENT

BACKGROUND OF THE INVENTION

The present invention relates to a mechanism for attaching a component to an instrument having variable geometry. More particularly, certain embodiments of the present invention relate to a universal attachment mechanism for attaching a surgical tracking device to a surgical instrument.

During surgical operations, it is beneficial to be able to track the direction and progress of a surgical instrument, such as a drill bit, into a patient's body in order to ensure that the instrument is directed into the appropriate point in the body. Therefore, surgical tracking systems have been developed that are able to display and monitor movement of a surgical instrument relative to an image of the patient's body.

One system used for surgical tracking is an electromagnetic tracking system. In a typical electromagnetic tracking system, the area of the patient's body where surgery is to take place is imaged using an imaging technology such as the MRI, X-ray, CT scan or any other appropriate imaging device. The scanned images are stored in a computer system and are displayed on a screen during the surgical procedure. A transmitter that emits an electromagnetic field is then secured to the patient's body proximate the area of the patient's body where surgery is to take place. The instrument that is to be tracked during surgery has a receiver attached thereto that receives the electromagnetic signals from the transmitter. The transmitter and receiver are both connected to the computer that displays the image. The computer translates the location of the transmitter on the patient's body to an equivalent point on the image. Then, by monitoring the signals sent from the transmitter to the receiver as the instrument is used in surgery, the computer is able to track the movement of the instrument relative to the transmitter and transpose the movement to the image. Therefore, medical personnel may closely track the positioning and progress of the instrument within the patient's body during surgery by examining the image.

Alternatively, in some electromagnetic systems, a receiver is placed on the patient and the instrument, and a field transmitter is placed proximate the patient. The receivers and transmitter are connected to the computer, and the computer is then able to track the movements of the instrument on an image similarly to the system using just a single receiver.

There are other surgical tracking systems besides electromagnetic tracking systems, such as optical tracking systems. Optical tracking systems typically use light emitting diodes (LEDs) that are attached to the surgical instrument and to the body portion of the patient on which the surgical procedure is to be performed. The LEDs are tracked by a camera unit (sometimes referred to as a digitizer). The output of the camera unit is used by the computer to recreate the movement of the instrument on the image.

In order for a surgical tracking system to work, the tracking device attached to the instrument, whether it be a receiver, transmitter or an LED, must be secured against movement relative to the instrument. If the tracking device moves relative to the instrument during surgery, the recreation of the instrument's position on the image will be incorrect. An incorrect tracking image may cause a surgeon to misdirect the instrument and possibly endanger the patient's health.

Since most surgical instruments are not provided with an integral tracking device, a separate attachment mechanism is generally used to retain a tracking device to the instrument. Many surgical instruments, such as drills, have traditionally been cylindrical in shape. As a result, a tracking device was often connected to the instrument by a cylindrical clamping mechanism, for example two C-shaped pieces connected at one by a hinge and at another end by a clasp. However, as ergonomic concerns have become increasingly prevalent in instrument design, the instruments have assumed more complex and contoured shapes. Many surgical instruments made today have a complex and variable geometry that cannot be accommodated by attachment mechanisms of such limited versatility as a conventional cylindrical clamp. Therefore, attachment mechanisms are often custom-made for each different kind of surgical instrument. In one common design, a boss is specifically developed for attachment to each surgical instrument, and the tracking device is then secured to the boss.

The practice of custom making surgical tracking attachment mechanisms has several drawbacks. First, the companies that make the attachment mechanisms must custom-design, develop, and market a new attachment mechanism specifically for each new surgical instrument that comes into the market. Thus, a company making attachment mechanisms must devote a significant amount of time and money to keeping up with new designs by the instrument makers. Companies that make the attachment mechanisms may, of course, work closely with the companies that make the surgical instruments in order that the instruments and the attachment mechanisms are compatible when the instruments come to market. However, this obligatory collaboration greatly slows down development and product-to-market time of the surgical instruments. Also, the companies that make the attachment mechanisms may be tied into different contracts with certain instrument makers and may be limited from making inroads into business with other instrument makers. An inability to fully reach into the instrument market is especially frustrating because recently there has been a significant increase in the number of new surgical applications, especially in orthopedics. Furthermore, even in instances where the same company makes the instrument and the attachment mechanism, the company must still invest the time and money into custom-designing and developing a new attachment mechanism for each surgical instrument, and therefore still has a delayed product-to-market time. Additionally, because of collaboration between instrument makers and attachment makers or instances where the same company makes the instrument, attachment mechanism, and tracking system, the end user may be limited to only using the tracking system of the company that makes the attachment mechanism for a particular instrument.

Therefore, a need exists for an improved attachment mechanism compatible for use with as many different instruments and tools as possible.

BRIEF SUMMARY OF THE INVENTION

Certain embodiments of the present invention include an attachment mechanism for attaching a component to an instrument. The attachment mechanism includes a first hoop assembly having a first hoop receiving a first portion of the instrument and a second hoop assembly having a second hoop receiving a second portion of the instrument. Either one of the first hoop assembly or the second hoop assembly may be configured to retain the component thereto. The first and second hoop assemblies are configured to be secured to each other such that the first and second hoops are in tension with, and secured about, the instrument.

Certain embodiments of the present invention include an attachment system. The attachment system includes an instrument having a body and a handle, a tracking device, and an attachment mechanism. The attachment mechanism has first and second hoop assemblies. The first hoop assembly includes a first hoop that receives a first portion of the body proximate a first side of the handle and the second hoop assembly includes a second hoop that receives a second portion of the body proximate a second side of the handle. Either one of the first or second hoop assemblies is configured to retain the tracking device thereto. The first and second hoop assemblies are configured to be secured to each other such that the first and second hoops are in tension with, and secured about, the body.

Certain embodiments of the present invention include an attachment mechanism for securing a component to an instrument. The instrument has a body portion with a first end, a second end, and a cross-sectional dimension that increases between the first and second ends. The attachment mechanism includes a first hoop positionable around the first end of the body portion and a second hoop positionable about the second end of the body portion. The attachment mechanism also includes a mechanism configured to secure the component to one of the first and second hoops. The attachment mechanism includes a connection mechanism configured to draw the first and second hoops toward each other such that the interface between the first and second hoops and the increasing cross-sectioned dimension of the body portion secures the first and second hoops relative to the body portion.

Certain embodiments of the present invention include an attachment mechanism for securing a component to an instrument. The instrument has a body portion with a first end, a second end, and a cross-sectional dimension that decreases between the first and second ends. The attachment mechanism includes a first hoop positionable around the first end of the body portion and a second hoop positionable about the second end of the body portion. The attachment mechanism also includes a mechanism configured to secure the component to one of the first and second hoops. The attachment mechanism further includes a connection mechanism configured to move the first and second hoops away from each other such that the interface between the first and second hoops and the decreasing cross-sectioned dimension of the body portion secures the first and second hoops relative to the body portion.

Certain embodiments of the present invention include a method for securing a component to an instrument where the instrument has a body portion with a first end and a second end. The method includes connecting the component to one of first and second hoops, engaging one of the first and second hoops to the instrument along the body portion from the first end, engaging the other of the first and second hoops to the instrument along the body portion from the second end, and securing the first and second hoops to each other such that the first and second hoops are drawn to each other and secured about the body portion.

Figure 1:
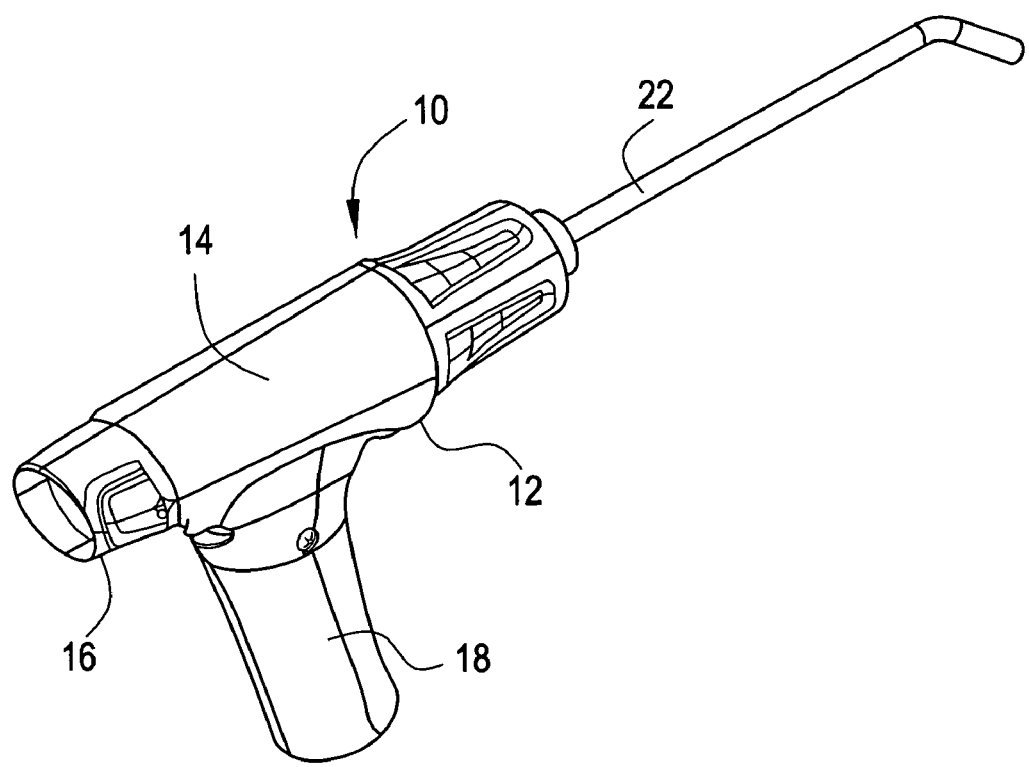
FIG. 1 is an isometric view of a conventional surgical instrument.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

FIG. 1 is an isometric view of a conventional surgical instrument 10. The instrument 10 has a main body 14, a handle 18 and a working portion 22. In the illustrated embodiment, the body portion is barrel-shaped but it can take a variety of other shapes. The body 14 has a front portion 12 on the front side of the handle 18 and a rear portion 16 on the rear side of the handle 18. The working portion 22 extends from the front portion 12 and may be removably connected thereto, e.g., via a chuck assembly (not shown). The rear portion 16 may house pneumatic and electrical components that drive the working portion 22 and provide irrigation and suction.

The body 14 and the handle 18 are contoured to provide an ergonomically desirable geometry and weight distribution such that the instrument 10 may comfortably be used in a surgeon's hand. The ergonomically motivated design, or variable geometry design, of the instrument 10 is typical for any number of different surgical instruments, for example, a drill. Furthermore, such a variable geometry design is typical for any number of different tools, instruments, appliances, or utensils, whether they be surgically related or not.

Figure 2:
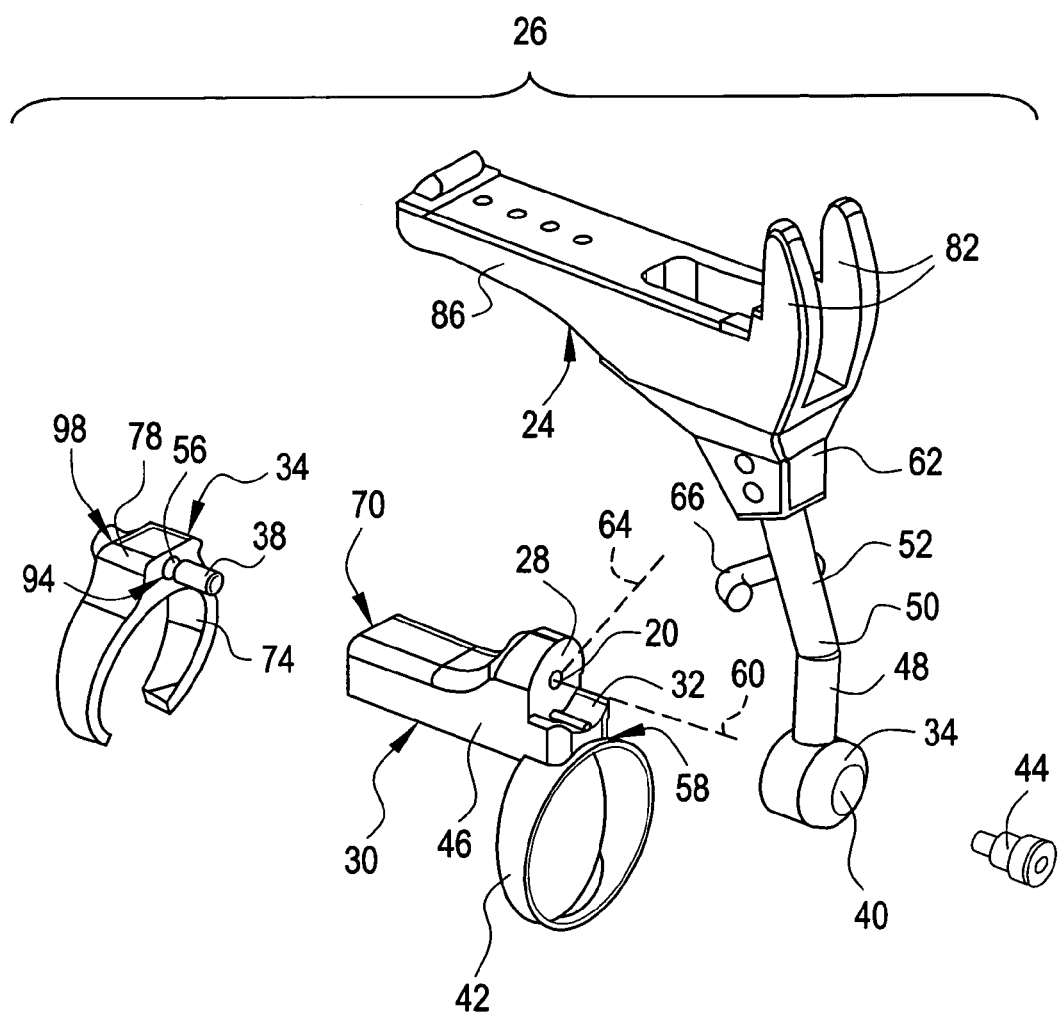
FIG. 2 is an exploded isometric view of an attachment mechanism formed according to an embodiment of the present invention.

FIG. 2 is an exploded isometric view of an attachment mechanism 26 formed according to an embodiment of the present invention. The attachment mechanism 26 includes a first or front hoop assembly 30, a second or rear hoop assembly 34, and an attachment assembly 24. The front hoop assembly 30 includes a ring-shaped first or front hoop 42 formed with a connector bar 46. The front hoop 42 is shown as a closed ring, but, alternatively, the front hoop 42 may be non-continuous, for example it may be open ended opposite the connector bar 46 such that it operates more like a clamp. By way of example and not by way of limitation, the front hoop 42 may be a ring or a clamp or a flexible, adjustable strap. The front hoop 42 extends from a bottom side of the connector bar 46 at a front end 58 thereof. The front hoop 42 has a fixed diameter generally large enough to receive the body portion of any number of different surgical instruments. Alternatively, the front hoop 42 may be adjustable such that the diameter can be varied to allow the front hoop to be tightly secured about a variety of points on an instrument body. The front hoop 42 has a thin wall such that it may be secured about the body of a surgical instrument and cause minimal interference with operation of the instrument. The front hoop 42 is made of a strong, flexible material that only minimally affects electromagnetic signals. For example, the front hoop 42 may be made of 300 series stainless steel, titanium, or certain polymers or composites.

The connector bar 46 generally extends along an axis perpendicular to the circumference of the front hoop 42. The connector bar 46 has a circular face 28 located behind an arced cut out 32 proximate the front end 58. A cylindrical threaded hole 20 extends through the face 28. The connector bar 46 also has a cylindrical, threaded hole (not shown) located at a back end 70 thereof.

The attachment assembly 24 includes a cylindrical support beam 50 that is connected to a cylindrical base 36 at one end and a tracking device carrier 62 at another end. The base 36 has a cylindrical hole 40 that is configured to receive a screw 44. The support beam 50 has a first portion 48 that extends upward perpendicularly from the base 36 and a second portion 52 that extends from the first portion 48 to the tracking device carrier 62 at an obtuse angle. Alternatively, the entire support beam 50 may be one straight beam that extends from the base 36 at any angle in any direction. Alternatively, the second portion 52 may extend from the first portion 48 at any angle in any direction. The tracking device carrier 62 has prongs 82 and a platform 86 that are configured to securably retain a surgical tracking device (not shown), such as an electromagnetic receiver or an optical tracking component such as an LED. The support beam 50 includes a hook 66 extending therefrom that retains a cord (not shown) extending from the tracking device held in the tracking device carrier 62. The tracking device carrier 62 is preferably made of a hard plastic in order to avoid interfering with electromagnetic signals being sent to the tracking device.

In operation, the attachment assembly 24 is connected to the front hoop assembly 30 by inserting the screw 44 through the hole 40 in the base 36 and the hole 20 in the face 28 and tightening the screw 44. When the screw 44 is completely inserted into the holes 40 and 20, the base 36 is retained within the cutout 32 along the face 28. The screw 44 is configured such that the base 36 may be rotated about the screw 44 within the cutout 32 without being loosened from the face 28. Thus, the attachment assembly 24 may be rotated about the front hoop assembly 30 in either direction along a longitudinal axis 60. Alternatively, or additionally, the attachment mechanism 26 may be configured such that the attachment assembly 24 may be rotated about the front hoop assembly 30 in either direction along a transverse axis 64. The attachment assembly 24 may be rotated isocentrically about the attachment mechanism 26 such that the relative distance does not change, or substantially change, between the tracking device and the longitudinal axis 60. Similarly, the attachment assembly 24 may be rotated isocentrically about the attachment mechanism 26 such that the relative distance does not change, or substantially change, between the tracking device and a longitudinal axis of the working portion 22 (FIG. 1) or a longitudinal axis of the body 14 (FIG. 1). By being able to rotate the attachment assembly 24 relative to the instrument 10 in such a way, a surgeon can move the attachment assembly 24 and the tracking device out of the way of other instruments without affecting the communication between the tracking device and the other surgical tracking components.

The rear hoop assembly 34 includes a ring-shaped second or rear hoop 74 formed with a square-shaped connector block 78. The rear hoop 74 extends from a bottom side of the connector block 78. The rear hoop 74 is open at one end and has a fixed diameter generally large enough to receive the body of any number of different surgical instruments. Alternatively, the rear hoop 74 may be a closed ring like the front hoop 42. By way of example and not by way of limitation, the rear hoop 74 may be a ring or a clamp or a flexible, adjustable strap. Alternatively, the rear hoop 74 may be adjustable such that the diameter can be varied to allow the rear hoop to be tightly secured about a variety of points on an instrument body. The rear hoop 74 has a thin wall such that it may be secured about the body of a surgical instrument and cause minimal interference with operation of the instrument. The rear hoop 74 is made of a strong, flexible material that only minimally affects electromagnetic signals. For example, the rear hoop 74 is preferably made of 300 series stainless steel, titanium, or certain polymers or composites.

The connector block 78 has a cylindrical, threaded hole 56 extending therethrough from a front end 94 to a back end 98. The threaded hole 56 is configured to receive a fastener screw 38. In operation, the fastener screw 38 is threaded through the back end of the hole 56 in the connector block 78, out of the front end of the hole 56, and into a reciprocal threaded hole (not shown) in the back end 70 of the connector bar 46 in order to secure the rear hoop assembly 34 to the front hoop assembly 30.

Figure 3:
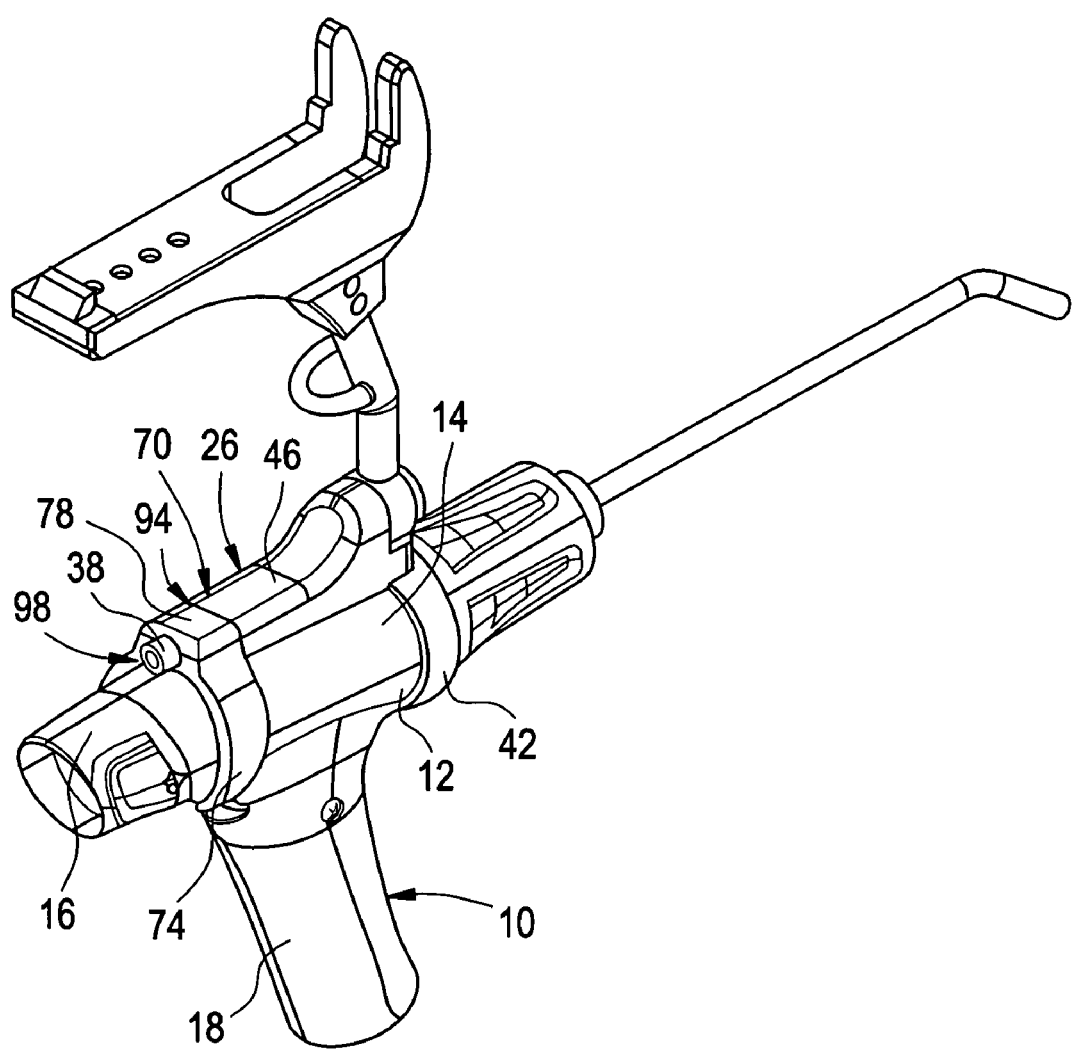
FIG. 3 is an isometric view of the attachment mechanism of FIG. 2 connected to the surgical instrument of FIG. 1.

FIG. 3 is an isometric view of the attachment mechanism 26 connected to the surgical instrument 10. In order to attach the attachment mechanism 26 to the surgical instrument 10, the front hoop 42 is slid along the front portion 12 of the body 14 with the connector bar 46 positioned along the top of the body 14. The front hoop 42 is slid along the front portion 12 toward the handle 18 until the diameter of the front hoop 42 prevents it from being slid any further. The rear hoop 74 is then slid along the rear portion 16 of the body 14 with the connector block 78 positioned along the top of the body 14. The rear hoop 74 is slid along the rear portion 16 toward the handle 18 until the diameter of the rear hoop 74 prevents it from being slid any further. The connector bar 46 and the connector block 78 are thus proximate each other, and the holes within the connector bar and block 46 and 78 are then aligned with each other. The fastener screw 38 is then threaded through the hole 56 (FIG. 2) in the connector block 78 from the back end 98 to the front end 94 and then into the hole at the back end 70 of the connector bar 46. The fastener screw 38 is threaded into the connector bar 46 until the connector bar 46 and the connector block 78 are tightly secured to each other. As the connector bar 46 and the connector block 78 are secured together with the fastener, the front and rear hoops 42 and 74 are pulled to each other and are in tension or "hoop stress" about their respective portions of the body 14. Thus, the flexible front and rear hoops 42 and 74 flex toward each other and are tightly secured to the body 14 of the surgical instrument 10 such that the attachment mechanism 26, and thus the tracking device, do not move relative to the surgical instrument 10.

Figure 4:
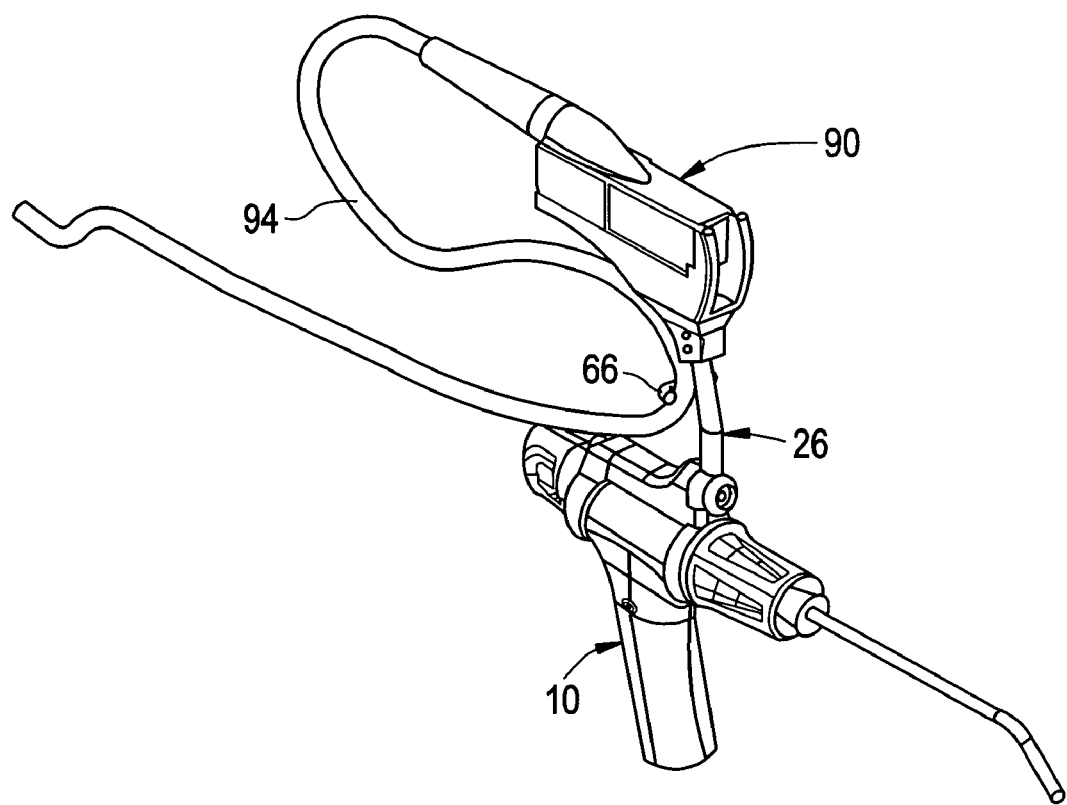
FIG. 4 is an isometric view of the attachment mechanism of FIG. 2 carrying a tracking device formed according to an embodiment of the present invention.

FIG. 4 is an isometric view of the attachment mechanism 26 carrying a tracking device 90 in the form of an electromagnetic receiver. Alternatively, the tracking device 90 may be an optical tracking component such as an LED, for example. An electrical cord 94 extends from the tracking device 90 through the hook 66 to a computer (not shown). The computer communicates with the tracking device 90 and a transmitter (not shown) positioned relative to the patient's body to recreate on an image of the patient's body the movement of the surgical instrument 10 relative to the transmitter in a conventional manner. This method of tracking the surgical instrument on the image allows medical personnel to track the progress of the surgical instrument 10 through the patient's body.

It should be noted that the attachment mechanism 26 may be used with instruments having a generally constant diameter or cylindrical body shape. The front and rear hoops 42 and 74 may both be slid onto the body such that the connector bar 46 and the connector block 78 are proximate each other. The connector bar 46 and the connector block 78 are then fastened to each other such that the front and rear hoops 42 and 74 are pulled toward each other and thus pulled in tension tightly against the body.

In an alternative embodiment, the attachment mechanism may be attached to an instrument body having a geometry that requires the front and rear hoops 42 and 74 to be pulled away from each other in order for the attachment mechanism to be secured to the instrument. By way of example and not by limitation, the attachment mechanism 26 may need to be attached to an instrument having an hourglass shaped body. In order to attach the attachment mechanism 26 to the surgical instrument 10, the front hoop 42 is slid along a first portion of the body from the center toward a first end until the diameter of the front hoop 42 prevents it from being slid any further. The rear hoop 74 is then slid along a second portion of the body from the center toward a second end until the diameter of the rear hoop 74 prevents it from being slid any further. The connector bar 46 and the connector block 78 are configured such that when fastened to each other, the front and rear hoops 42 and 74 are moved away from each other and are in tension or "hoop stress" about their respective portions of the body. Thus, the flexible front and rear hoops 42 and 74 flex away from each other and are tightly secured to the opposite ends of the hourglass shaped body.

In an alternative embodiment, the front and rear hoops 42 and 74 may be adjustable such that their diameters can be altered to accommodate instruments of varying body diameter. By way of example only, the front and rear hoops 42 and 74 may be adjustable hose clamps. By being able to change the diameter of the front and rear hoops 42 and 74, less tension is necessary between the front and rear hoop assemblies 30 and 34 to securely tighten the front and rear hoops 42 and 74 to the body of an instrument. Alternatively, the attachment mechanism 26 may include more than two hoops that receive a portion of an instrument. Alternatively, the attachment mechanism 26 may be configured to be attached to portions of an instrument besides the body, for example, the attachment mechanism 26 may be configured to be attached to the handle. Alternatively, the hoops of the attachment mechanism 26 do not have to be round or ring-shaped but may be any number of other shapes, for example, square, oval, or cylindrical, so long as the hoops are able to receive a portion of an instrument. Furthermore, the hoops of the attachment mechanism 26 need not be closed, but may be open ended. For example, the hoops may be open-ended clamps having legs that tightly engage the body of an instrument.

In an alternative embodiment, the support beam 50 connected to the tracking device carrier 62 may be connected to the rear hoop assembly 34 instead of the front hoop assembly 30. Also, in an alternative embodiment, the front hoop assembly 34 may include the short connector block 78 and the rear hoop assembly 34 may include the longer connector bar 46.

Alternatively, the front and rear hoop assemblies 30 and 34 may be secured to each other by a means other than the fastener screw 38 being inserted into the holes. In alternative embodiments, the front and rear hoop assemblies 30 and 34 may be connected by bolts, pins, straps, clamps, or any other number of fastening devices that can be used to secure the front and rear hoop assemblies 30 and 34 to each other. For example, in one alternative embodiment, the connector bar 46 and connector block 78 may have holes along the sides thereof and be configured to overlap such that the holes are aligned to receive a fastening pin.

Alternatively, the attachment mechanism 26 may be configured to secure any number of different surgical tracking devices to the surgical instrument 10. For example, the tracking device carrier 62 may be configured to retain an LED for use with an optical surgical tracking system. Further, the attachment mechanism 26 may be used to secure any component (not necessarily a tracking device) to any number of different tools, instruments, utensils, or appliances, whether they be surgically related or not. In other words, the attachment mechanism 26 may be configured to be used with any instrument having a variable geometry that is to be securely connected to another component. For example, the attachment mechanism 26 may be used to connect a component to a power drill or even a scope to a gun barrel.

The attachment mechanism of the different embodiments confers a number of benefits. The two connectable hoops allow the attachment mechanism to be used with instruments of different contours and varying diameters and geometry. The applicability of the attachment mechanism to different instruments of varying geometry can perhaps best be demonstrated with the example of using the attachment mechanism with a football. A football is shaped to have a single maximum radius at the center and a nearly infinite number of radius minima on either side of the center of the football (for example, along the parallel white stripes on the football). That is to say, the football has a cross-sectional dimension that increases between the opposite ends thereof. The variable geometry of the football makes it difficult to secure one clamp on the football, even if the clamp was at the maximum radius at the center, because the clamp could easily slide off. However, two clamps can be placed at equivalent radius minima on opposite sides of the center (such as along the stripes) and pulled or drawn toward each other such that the interface between the clamps and the increasing cross-sectioned dimension of the football secures the clamps relative to the football. In other words, the clamps are in tension at the radius minima and thus secured to the football.

The universal applicability of the attachment mechanism is a significant commercial advantage because attachment mechanisms no longer have to be custom made for every new instrument that comes into the market. One attachment mechanism may be used with all instruments and therefore no collaboration is necessary between different companies making instruments and attachment mechanisms. Additionally, the end user is no longer required to use the surgical tracking device of the same company that makes an attachment mechanism for a specific instrument.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An attachment mechanism for attaching a component to an instrument, comprising:
    a first hoop assembly having a first hoop receiving a first portion of the instrument;
    a second hoop assembly having a second hoop receiving a second portion of the instrument, either one of said first hoop assembly or said second hoop assembly being configured to retain the component thereto, said first and second hoop assemblies being configured to be secured to each other such that said first and second hoops are in tension with, and secured about, the instrument; and
    wherein the component is a surgical tracking device and the instrument is a surgical instrument.

2. The attachment mechanism of claim 1, further including a fastening screw that is received in said first and second hoop assemblies to secure said first and second hoop assemblies to each other such that said first and second hoops are either pulled toward each other or moved away from each other.

3. The attachment mechanism of claim 1, wherein said first hoop assembly includes a connector bar connected to said first hoop and said second hoop assembly includes a connector block connected to said second hoop, said connector block and said connector bar being configured to be secured to each other.

4. The attachment mechanism of claim 1, wherein said first hoop assembly includes a connector bar connected on one side to said first hoop and connected on another side to a support beam that is connected to a carrier securably receiving the component.

5. The attachment mechanism of claim 1, wherein said first hoop assembly includes a connector bar from which extends a support beam that is connected to a carrier securably receiving the component, said support beam being rotatable about said connector bar such that the relative distance between the component and a longitudinal axis of the instrument remains substantially the same.

6. The attachment mechanism of claim 1, wherein said first and second hoops are adjustable such that their diameters may be varied to receive portions of instruments of varying diameter.

7. The attachment mechanism of claim 1, wherein either or both of said first and second hoops are open ended clamps that receive the instrument.

8. An attachment system comprising:
    an instrument having a body and a handle;
    a tracking device; and
    an attachment mechanism, said attachment mechanism having first and second hoop assemblies, said first hoop assembly having a first hoop that receives a first portion of said body proximate a first side of said handle and said second hoop assembly having a second hoop that receives a second portion of said body proximate a second side of said handle, either one of said first or second hoop assemblies being configured to retain said tracking device thereto, said first and second hoop assemblies being configured to be secured to each other such that said first and second hoops are in tension with, and secured about, said body.

9. The attachment mechanism of claim 8, further including a fastening screw that is received in said first and second hoop assemblies to secure said first and second hoop assemblies to each other such that said first and second hoops are either pulled toward each other or moved away from each other.

10. The attachment mechanism of claim 8, wherein said first hoop assembly includes a connector bar connected to said first hoop and said second hoop assembly includes a connector block connected to said second hoop, said connector block and said connector bar being configured to be secured to each other.

11. The attachment mechanism of claim 8, wherein said first hoop assembly includes a connector bar from which extends a support beam that is connected to a carrier securably receiving said tracking device, said support beam being rotatable about said connector bar such that the relative distance between the tracking device and a longitudinal axis of said instrument remains substantially the same.

12. The attachment mechanism of claim 8, wherein said first and second hoops are adjustable such that their diameters may be altered to receive portions of said body where said body has a varying diameter.

13. The attachment mechanism of claim 8, wherein either or both of said first and second hoops are open-ended clamps that receive said body of said instrument.

14. The attachment mechanism of claim 8, wherein said instrument is a surgical instrument and said tracking device is a receiver used in an electromagnetic surgical tracking system.

15. The attachment mechanism of claim 8, wherein said tracking device is a light emitting diode used in an optical surgical tracking system.

16. An attachment mechanism for securing a component to an instrument, the instrument having a body portion with a first end, a second end, and a cross-sectional dimension that increases between the first and second ends, comprising:
    a first hoop positionable around the first end of the body portion;
    a second hoop positionable about the second end of the body portion;
    a mechanism configured to secure the component to one of said first and second hoops; and
    a connection mechanism configured to draw said first and second hoops toward each other such that the interface between said first and second hoops and the increasing cross-sectioned dimension of the body portion secures said first and second hoops relative to the body portion.

17. An attachment mechanism for securing a component to an instrument, the instrument having a body portion with a first end, a second end, and a cross-sectional dimension that decreases between the first and second ends, comprising:
    a first hoop positionable around the first end of the body portion;
    a second hoop positionable about the second end of the body portion;
    a mechanism configured to secure the component to one of said first and second hoops; and
    a connection mechanism configured to move said first and second hoops away from each other such that the interface between said first and second hoops and the decreasing cross-sectioned dimension of the body portion secures said first and second hoops relative to the body portion.

18. A method for securing a component to an instrument where the instrument has a body portion with a first end and a second end, comprising:

connecting the component to one of first and second hoops;

engaging one of said first and second hoops to the instrument along the body portion from the first end;

engaging the other of said first and second hoops to the instrument along the body portion from the second end;

securing said first and second hoops to each other such that said first and second hoops are drawn to each other and secured about the body portion; and fastening said first and second hoops to each other with a screw.

* * * * *